(12) United States Patent
Askem et al.

(10) Patent No.: US 11,285,047 B2
(45) Date of Patent: Mar. 29, 2022

(54) WOUND DRESSINGS AND METHODS OF USE WITH INTEGRATED NEGATIVE PRESSURE SOURCE HAVING A FLUID INGRESS INHIBITION COMPONENT

(71) Applicant: Smith & Nephew PLC, Watford (GB)

(72) Inventors: Ben Alan Askem, Brough (GB); Victoria Beadle, Hull (GB); John Philip Gowans, Hessle (GB); Mark Hesketh, Royston (GB); Allan Kenneth Frazer Grugeon Hunt, Beverley (GB); William Kelbie, Inverness (GB); Damyn Musgrave, Cottenham (GB); Joseph William Robinson, Papworth Everard (GB)

(73) Assignee: Smith & Nephew PLC, Watford (GB)

( * ) Notice: Subject to any disclaimer, the term of this patent is extended or adjusted under 35 U.S.C. 154(b) by 593 days.

(21) Appl. No.: 16/096,266

(22) PCT Filed: Apr. 26, 2017

(86) PCT No.: PCT/EP2017/059883
§ 371 (c)(1),
(2) Date: Oct. 24, 2018

(87) PCT Pub. No.: WO2017/186771
PCT Pub. Date: Nov. 2, 2017

(65) Prior Publication Data
US 2019/0159938 A1    May 30, 2019

Related U.S. Application Data

(60) Provisional application No. 62/327,676, filed on Apr. 26, 2016.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/784* (2021.05); *A61M 1/962* (2021.05)

(58) Field of Classification Search
CPC .......... A61F 13/00068; A61F 13/0216; A61M 1/784; A61M 1/962; A61M 1/90; A61M 1/915
See application file for complete search history.

(56) References Cited

U.S. PATENT DOCUMENTS 3,874,387 A    4/1975 Barbieri
4,224,941 A    9/1980 Stivala
(Continued)

FOREIGN PATENT DOCUMENTS

CN    201664463 U    12/2010
DE    198 44 355     4/2000
(Continued)

OTHER PUBLICATIONS

International Search Report and Written Opinion, re PCT Application No. PCT/EP2017/059883, dated Jul. 7, 2017.
(Continued)

*Primary Examiner* — Adam Marcetich
(74) *Attorney, Agent, or Firm* — Knobbe, Martens, Olson & Bear, LLP

(57) ABSTRACT

Disclosed embodiments relate to apparatuses and methods for wound treatment. In some embodiments, a negative pressure source is incorporated into a wound dressing apparatus so that the wound dressing and the negative pressure source are part of an integral or integrated wound dressing
(Continued)

structure that applies the wound dressing and the negative pressure source simultaneously to a patient's wound. The negative pressure source and/or electronic components may be positioned between a wound contact layer and a cover layer of the wound dressing. A component may be used to prevent wound exudate from contacting the inlet of the negative pressure source.

25 Claims, 11 Drawing Sheets

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,209,541 B1 | 4/2001 | Wallace |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| D625,422 S | 10/2010 | Arbesman et al. |
| 7,837,673 B2 | 11/2010 | Vogel |
| 7,838,717 B2 | 11/2010 | Haggstrom et al. |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,118,794 B2 | 2/2012 | Weston et al. |
| 8,158,844 B2 | 4/2012 | McNeil |
| 8,167,869 B2 | 5/2012 | Wudyka |
| 8,207,392 B2 | 6/2012 | Haggstrom et al. |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,444,612 B2 | 5/2013 | Patel et al. |
| 8,449,508 B2 | 5/2013 | Coulthard et al. |
| 8,460,255 B2 | 6/2013 | Joshi et al. |
| 8,500,776 B2 | 8/2013 | Ebner |
| 8,529,548 B2 | 9/2013 | Blott et al. |
| 8,545,464 B2 | 10/2013 | Weston |
| 8,545,466 B2 | 10/2013 | Andresen et al. |
| 8,569,566 B2 | 10/2013 | Blott et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,628,505 B2 | 1/2014 | Weston |
| 8,641,691 B2 | 2/2014 | Fink |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,829,263 B2 | 9/2014 | Haggstrom et al. |
| 8,870,837 B2 | 10/2014 | Locke et al. |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,050,209 B2 | 6/2015 | Coulthard et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,168,330 B2 | 10/2015 | Joshi et al. |
| 9,198,802 B2 | 12/2015 | Robinson et al. |
| 9,220,822 B2 | 12/2015 | Hartwell et al. |
| 9,259,558 B2 | 2/2016 | Tsai |
| 9,265,665 B2 | 2/2016 | Robinson et al. |
| 9,265,867 B2 | 2/2016 | Coulthard et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,452,245 B2 | 9/2016 | Jaeb et al. |
| 9,560,975 B2 | 2/2017 | Mei et al. |
| 9,629,986 B2 | 4/2017 | Patel et al. |
| D787,690 S | 5/2017 | Mackay et al. |
| 9,669,138 B2 | 6/2017 | Joshi et al. |

(56) References Cited

U.S. PATENT DOCUMENTS

| | | |
|---|---|---|
| 9,737,649 B2 | 8/2017 | Begin et al. |
| 9,770,368 B2 | 9/2017 | Robinson et al. |
| 9,795,725 B2 | 10/2017 | Joshi et al. |
| 9,814,811 B2 | 11/2017 | Aalders et al. |
| 9,844,475 B2 | 12/2017 | Hartwell |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,016,309 B2 | 7/2018 | Hartwell |
| 10,016,544 B2 | 7/2018 | Coulthard et al. |
| 10,046,095 B1 | 8/2018 | Middaugh et al. |
| 10,046,096 B2 | 8/2018 | Askem et al. |
| 10,086,117 B2 | 10/2018 | Locke et al. |
| 10,238,777 B2 | 3/2019 | Arthur et al. |
| 2003/0060750 A1* | 3/2003 | Van Der Linden .. A61G 13/108 604/26 |
| 2003/0212357 A1 | 11/2003 | Pace |
| 2004/0064132 A1 | 4/2004 | Boehringer et al. |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119607 A1* | 6/2005 | Van Der Linden .... A61B 90/40 604/23 |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0213527 A1 | 9/2006 | Argenta et al. |
| 2006/0259102 A1 | 11/2006 | Slatkine |
| 2007/0055209 A1 | 3/2007 | Patel et al. |
| 2007/0057389 A1* | 3/2007 | Davis ........................ C02F 1/78 261/122.1 |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2007/0265585 A1* | 11/2007 | Joshi ..................... A61M 1/962 604/313 |
| 2007/0265586 A1 | 11/2007 | Joshi et al. |
| 2008/0021356 A1 | 1/2008 | Castello Escude |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2011/0028918 A1* | 2/2011 | Hartwell ............... A61F 13/025 604/319 |
| 2011/0054421 A1* | 3/2011 | Hartwell ................. A61M 1/90 604/319 |
| 2011/0071483 A1* | 3/2011 | Gordon .................. A61M 1/73 604/319 |
| 2011/0092927 A1 | 4/2011 | Wilkes et al. |
| 2011/0112492 A1 | 5/2011 | Bharti et al. |
| 2011/0224631 A1 | 9/2011 | Simmons |
| 2011/0282309 A1* | 11/2011 | Adie ........................ A61M 1/84 604/319 |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0035649 A1* | 2/2013 | Locke ............... A61F 13/00068 604/290 |
| 2013/0090615 A1 | 4/2013 | Jaeb et al. |
| 2013/0102979 A1 | 4/2013 | Coulthard et al. |
| 2013/0123723 A1 | 5/2013 | Tout et al. |
| 2013/0190706 A1* | 7/2013 | Kleiner ............ A61F 13/00068 604/319 |
| 2013/0215638 A1 | 8/2013 | Dabov et al. |
| 2014/0100536 A1 | 4/2014 | Angel |
| 2014/0163490 A1 | 6/2014 | Locke et al. |
| 2014/0228786 A1* | 8/2014 | Croizat ................... A61F 13/53 604/319 |
| 2014/0296805 A1* | 10/2014 | Arthur .................. A61M 1/784 604/319 |
| 2014/0330227 A1 | 11/2014 | Coulthard et al. |
| 2014/0343518 A1 | 11/2014 | Riesinger |
| 2014/0350494 A1* | 11/2014 | Hartwell ........... A61F 13/00068 604/319 |
| 2015/0057625 A1 | 2/2015 | Coulthard et al. |
| 2015/0065965 A1 | 3/2015 | Haggstrom et al. |
| 2015/0141941 A1* | 5/2015 | Allen ................ A61F 13/00068 604/319 |
| 2015/0157784 A1* | 6/2015 | Santora ............... A61M 1/0058 604/35 |
| 2015/0202354 A1 | 7/2015 | Wall |
| 2015/0224238 A1 | 8/2015 | Hartwell |
| 2015/0258256 A1 | 9/2015 | Jaeb et al. |
| 2015/0250931 A1 | 10/2015 | Bharti et al. |
| 2016/0015873 A1 | 1/2016 | Robinson et al. |
| 2016/0058927 A1 | 3/2016 | Weston |
| 2016/0166438 A1 | 6/2016 | Rovaniemi |
| 2016/0199546 A1 | 7/2016 | Chao |
| 2016/0206793 A1 | 7/2016 | Robinson et al. |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0304510 A1 | 10/2017 | Askem et al. |
| 2017/0319761 A1 | 11/2017 | Locke et al. |
| 2017/0326277 A1 | 11/2017 | Huang |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0042521 A1* | 2/2018 | Ryu ..................... A61B 5/1073 |
| 2018/0104393 A1 | 4/2018 | Wu et al. |
| 2018/0200414 A1 | 7/2018 | Askem et al. |
| 2018/0296397 A1 | 10/2018 | Askem et al. |
| 2018/0311078 A1 | 11/2018 | Hartwell |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0125943 A1 | 5/2019 | Askem et al. |
| 2019/0143007 A1 | 5/2019 | Askem et al. |
| 2019/0192350 A1 | 6/2019 | Gowans et al. |
| 2019/0282737 A1 | 9/2019 | Beadle et al. |
| 2020/0022846 A1 | 1/2020 | Beadle et al. |

FOREIGN PATENT DOCUMENTS

| | | |
|---|---|---|
| EP | 0512543 A2 | 11/1992 |
| EP | 1411874 A1 | 4/2004 |
| EP | 1512452 A1 | 3/2005 |
| EP | 1455701 B1 | 3/2006 |
| EP | 1448261 B1 | 2/2007 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2340064 A1 | 7/2011 |
| EP | 2346468 A2 | 7/2011 |
| EP | 2349155 A2 | 8/2011 |
| EP | 1814609 B2 | 9/2011 |

(56) References Cited

FOREIGN PATENT DOCUMENTS

| | | |
|---|---|---|
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2 345 437 | 4/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 3 072 542 | 9/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2939320 A1 | 6/2010 |
| GB | 2511523 A | 9/2014 |
| RU | 131622 U1 | 8/2013 |
| WO | WO-2007030601 A2 | 3/2007 |
| WO | WO 2009/098696 | 8/2009 |
| WO | WO-2009120951 A2 | 10/2009 |
| WO | WO 2011/130570 | 10/2011 |
| WO | WO 2011/135285 | 11/2011 |
| WO | WO-2011144888 A1 | 11/2011 |
| WO | WO 2012/057881 | 5/2012 |
| WO | WO 2013/136181 | 9/2013 |
| WO | WO 2013/175306 | 11/2013 |
| WO | WO 2014/099709 | 6/2014 |
| WO | WO 2016/103031 | 6/2016 |
| WO | WO-2016126560 A1 | 8/2016 |
| WO | WO 2016/182977 | 11/2016 |
| WO | WO 2017/079174 | 5/2017 |
| WO | WO 2017/153357 | 9/2017 |
| WO | WO 2017/186771 | 11/2017 |
| WO | WO 2017/191154 | 11/2017 |
| WO | WO-2017196888 A1 | 11/2017 |
| WO | WO-2018056060 A1 | 3/2018 |
| WO | WO-2018115461 A1 | 6/2018 |
| WO | WO-2018156730 A1 | 8/2018 |
| WO | WO 2018/164803 | 9/2018 |
| WO | WO-2018158250 A1 | 9/2018 |
| WO | WO-2018162613 A1 | 9/2018 |
| WO | WO-2018185138 A1 | 10/2018 |
| WO | WO-2018187394 A1 | 10/2018 |
| WO | WO-2018192978 A1 | 10/2018 |

OTHER PUBLICATIONS

International Preliminary Report on Patentability, re PCT Application No. PCT/EP2017/059883, dated Nov. 8, 2018.

* cited by examiner

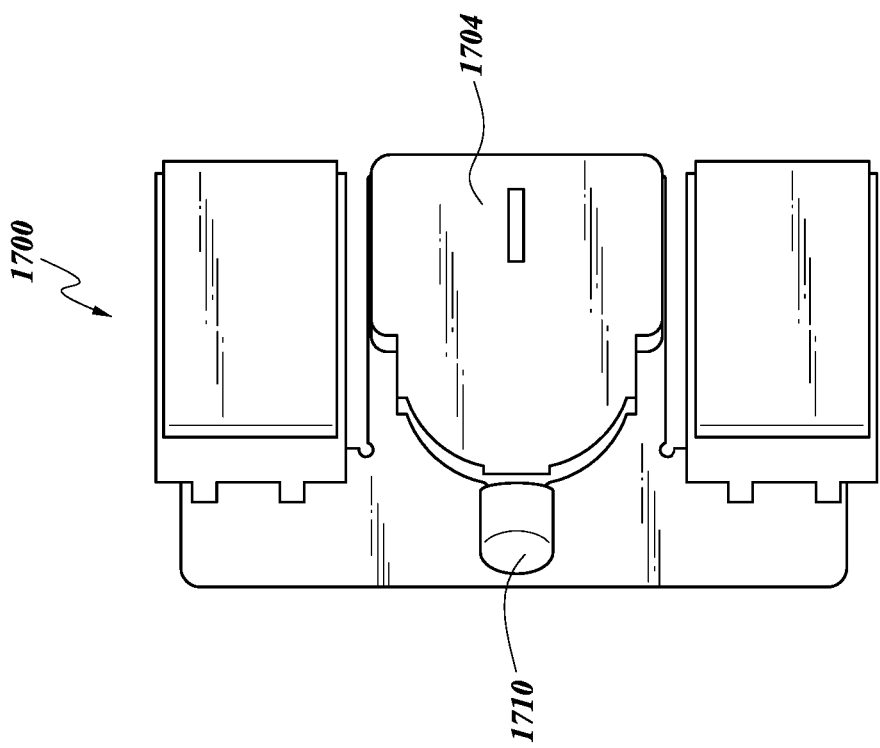
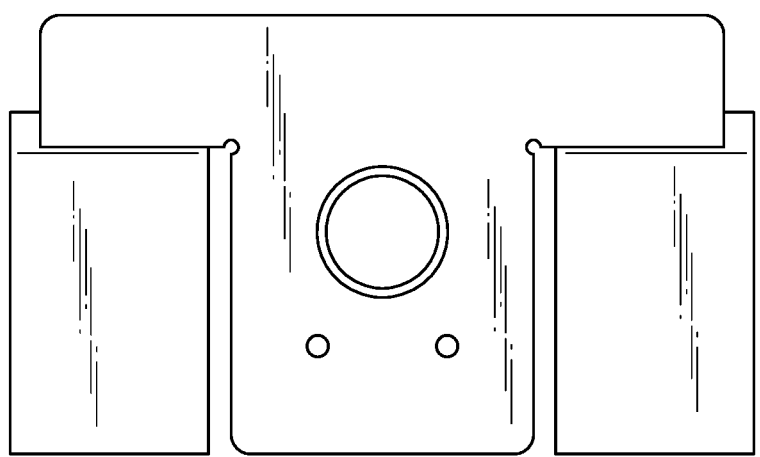

WOUND DRESSINGS AND METHODS OF USE WITH INTEGRATED NEGATIVE PRESSURE SOURCE HAVING A FLUID INGRESS INHIBITION COMPONENT

CROSS-REFERENCE TO RELATED APPLICATIONS

This application is a U.S. national stage application of International Patent Application No. PCT/EP2017/059883, filed Apr. 26, 2017, which claims priority to U.S. Provisional Application No. 62/327,676, filed Apr. 26, 2016, which is hereby incorporated by reference in its entirety.

BACKGROUND

Technical Field

Embodiments described herein relate to apparatuses, systems, and methods for the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Prior art dressings for use in negative pressure such as those described above have included a negative pressure source located in a remote location from the wound dressing. Negative pressure sources located remote from the wound dressing have to be held by or attached to the user or other pump support mechanism. Additionally, a tubing or connector is required to connect the remote negative pressure source to the wound dressing. The remote pump and tubing can be cumbersome and difficult to hide in or attach to patient clothing. Depending on the location of the wound dressing, it can be difficult to comfortably and conveniently position the remote pump and tubing. When used, wound exudate may soak into the dressing, and the moisture from the wound has made it difficult to incorporate electronic components into the dressing.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, a negative pressure source is incorporated into a wound dressing apparatus so that the wound dressing and the negative pressure source are part of an integral or integrated wound dressing structure that applies the wound dressing and the negative pressure source simultaneously to a patient's wound. The negative pressure source and/or electronic components may be positioned between a wound contact layer and a cover layer of the wound dressing. A component may be used to prevent wound exudate from contacting the inlet of the negative pressure source. These and other embodiments as described herein are directed to overcoming particular challenges involved with incorporating a negative pressure source and/or electronic components into a wound dressing.

In some aspects, a wound dressing apparatus comprises a wound dressing configured to be positioned over a wound site, the wound dressing comprising a wound contact layer configured to be positioned in contact with a wound, a first area and a second area positioned adjacent to the first area, wherein the first area comprises an absorbent material and the second area is configured to receive a negative pressure source, and a cover layer configured to cover and form a seal over the wound contact layer, the first area, and the second area, a negative pressure source disposed on or positioned within the second area of the wound dressing, the negative pressure source comprising an inlet and an outlet and being operable to apply negative pressure to the wound site, and a component in fluid communication with the inlet, the component defining a plurality of flow paths between an interior of the wound dressing and the inlet such that occlusion of the inlet is inhibited, and wherein the component is in fluid communication with the absorbent material and configured to inhibit flow of wound exudate from the wound site into the inlet.

The apparatus of the preceding paragraph may also include any combination of the following features described in this paragraph, among others described herein. Each of the features described in the following paragraphs may also be part of another embodiment that does not necessarily include all of the features of the previous paragraph. The component can comprise a hydrophobic material configured to repel wound exudate. The component can comprise a material having a pore size configured to resist ingress of wound exudate due to capillary action. The component can comprise one or more porous polymer molded components. The polymer comprising the one or more porous polymer molded components can be hydrophobic and can have a pore size in the range of approximately 20 microns to approximately 40 microns. The pore size can be approximately 30 microns. The polymer comprising the one or more porous polymer molded components can be hydrophobic and can have a pore size in the range of approximately 5 microns to approximately 40 microns. The pore size can be approximately 10 microns.

The polymer can be POREX® or PORVAIR®. The polymer can be one of hydrophobic polyethylene or hydrophobic polypropylene. Each of the one or more porous polymer molded components can be configured to increase the contact area between the pump inlet and the interior of the wound dressing. The one or more porous polymer components have a three-dimensional shape. For example, the one or more porous polymer components can be crescent-shaped, thimble-shaped, or cuboid or generally cuboid shaped. The one or more porous polymer components can also have curved or beveled corners and/or edges. The one or more porous polymer components can be configured to attach to at least one of the inlet and an end of a tubular extension in fluid communication with the inlet and the interior of the wound dressing.

The component can comprise one or more micro porous membranes attached to the inlet. The wound dressing apparatus can comprise a spacer material disposed within the membrane, the spacer material configured to inhibit the membrane from collapsing. The micro porous membrane can comprise Versapore having a 0.2 micron pore size (Pall). The component can comprise one or more lengths of fine bore tubing defining a plurality of holes along their lengths. The one or more lengths of fine bore tubing can form one or more loops between the inlet and the wound dressing. The one or more lengths of fine bore tubing can extend from the inlet to one or more different points in the wound dressing. The negative pressure source can be a micro pump. The wound dressing apparatus can comprise a controller configured to control the operation of the micro pump to apply negative pressure to the wound site. The absorbent material can be configured to absorb wound exudate. The component can be attached to the inlet. The component can be fitted to the inlet.

In one embodiment, a wound dressing apparatus comprises a wound dressing configured to be positioned over a wound site, a negative pressure source disposed on or positioned within the wound dressing, the negative pressure source comprising an inlet and an outlet and being operable to apply negative pressure to the wound site, and a porous polymer component fitted to the inlet of the negative pressure source and in fluid communication with the inlet, the porous polymer component comprising a three-dimensional body defining a plurality of flow paths between an interior of the wound dressing and the inlet such that occlusion of the inlet is inhibited.

The porous polymer component can comprise a hydrophobic material configured to repel wound exudate. The porous polymer component can have a pore size in the range of approximately 20 microns to approximately 40 microns. The pore size can be approximately 30 microns. The porous polymer component can have a pore size in the range of approximately 5 microns to approximately 40 microns. The pore size can be approximately 10 microns. The polymer can be PORVAIR Vyon®. The porous polymer component can be crescent-shaped, thimble-shaped, or cuboid or generally cuboid shaped. The porous polymer component can also have curved or beveled corners and/or edges.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 7A illustrates the top view of an electronics unit including a pump and a component directly coupled to the pump inlet;

FIG. 7B illustrates a bottom or wound facing surface of an electronics unit including a pump and a component directly coupled to the pump inlet;

DETAILED DESCRIPTION

Figure 1:
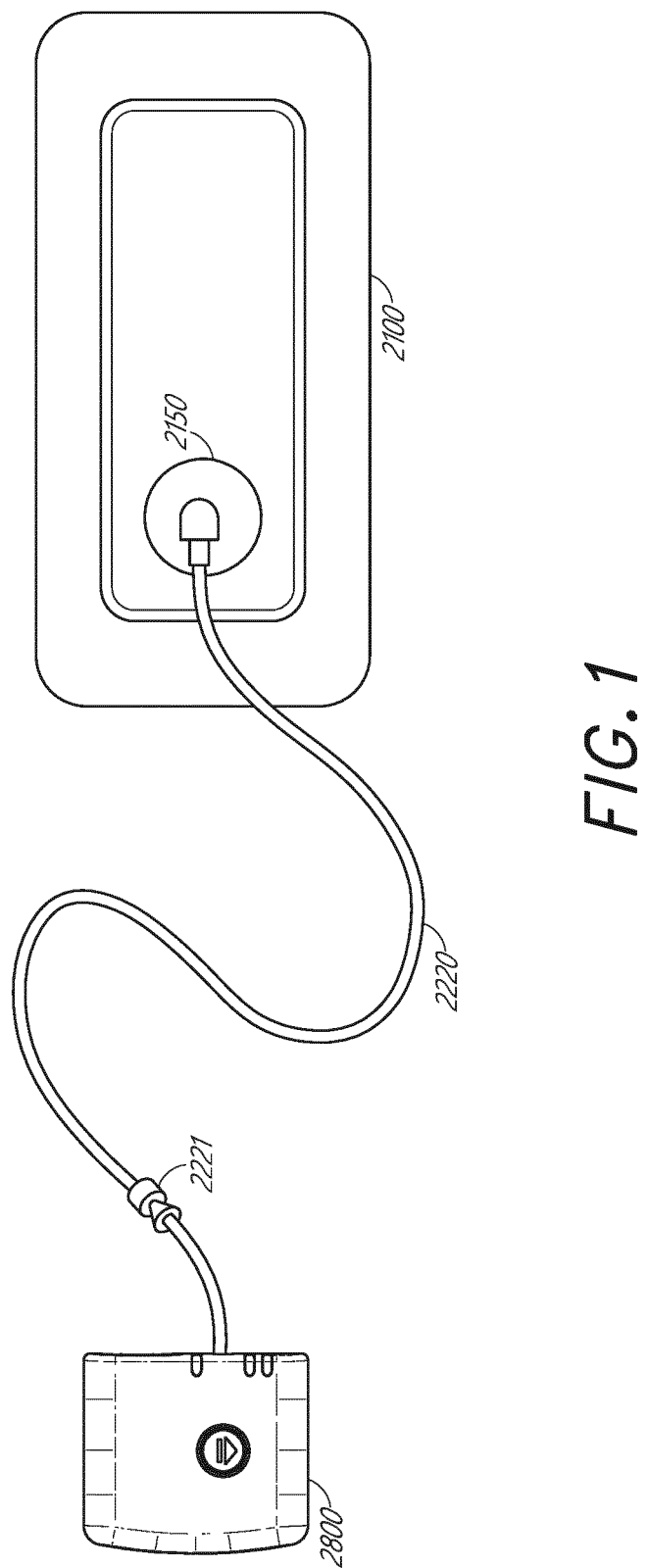
FIG. 1 illustrates an embodiment of a wound treatment apparatus including a wound dressing in combination with a pump.

Embodiments disclosed herein relate to apparatuses and methods of treating a wound with reduced pressure, including a source of negative pressure and wound dressing components and apparatuses. The apparatuses and components including the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also, in other embodiments, a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in U.S. Provisional Application No. 61/650,904, filed May 23, 2012, titled "APPARATUSES AND METHODS FOR NEGATIVE PRESSURE WOUND THERAPY," International Application No. PCT/IB2013/001469, filed May 22, 2013, titled "APPARATUSES AND METHODS FOR NEGATIVE PRESSURE WOUND THERAPY," and published as WO 2013/175306 on Nov. 28, 2013, U.S. patent application Ser. No. 14/418,874, filed Jan. 30, 2015, published as U.S. Publication No. 2015/0216733, published Aug. 6, 2015, titled "WOUND DRESSING AND METHOD OF TREATMENT," U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT," U.S. patent application Ser. No. 14/658,068, filed Mar. 13, 2015, U.S. Application No. 2015/0182677, published Jul. 2, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as US2011/0282309, titled "WOUND DRESSING AND METHOD OF USE," and which is hereby incorporated by reference in its entirety, including further details relating to embodiments of wound dressings, the wound dressing components and principles, and the materials used for the wound dressings. Additionally, the present application is related to U.S. Provisional Application No. 62/304,790, filed Mar. 7, 2016, titled "REDUCED PRESSURE APPARATUSES AND METHODS, the subject matter of which is considered to be part of this application and is included in the Appendix below.

FIG. 1 illustrates an embodiment of a TNP wound treatment including a wound dressing 2100 in combination with a pump 2800. As stated above, the wound dressing 2100 can be any wound dressing embodiment disclosed herein or have any combination of features of any number of wound dressing embodiments disclosed herein. Here, the dressing 2100 may be placed over a wound, and a conduit 2220 may then be connected to a port 2150, although in some embodiments the dressing 2100 may be provided with at least a portion of the conduit 2220 preattached to the port 2150. Preferably, the dressing 2100 is provided as a single article with all wound dressing elements (including the port 2150) pre-attached and integrated into a single unit. The wound dressing 2100 may then be connected, via the conduit 2220, to a source of negative pressure such as the pump 2800. The pump 2800 can be miniaturized and portable, although larger conventional pumps may also be used with the dressing 2100. In some embodiments, the pump 2800 may be attached or mounted onto or adjacent the dressing 2100. A connector 2221 may also be provided so as to permit the conduit 2220 leading to the wound dressing 2100 to be disconnected from the pump, which may be useful for example during dressing changes.

Figure 2:
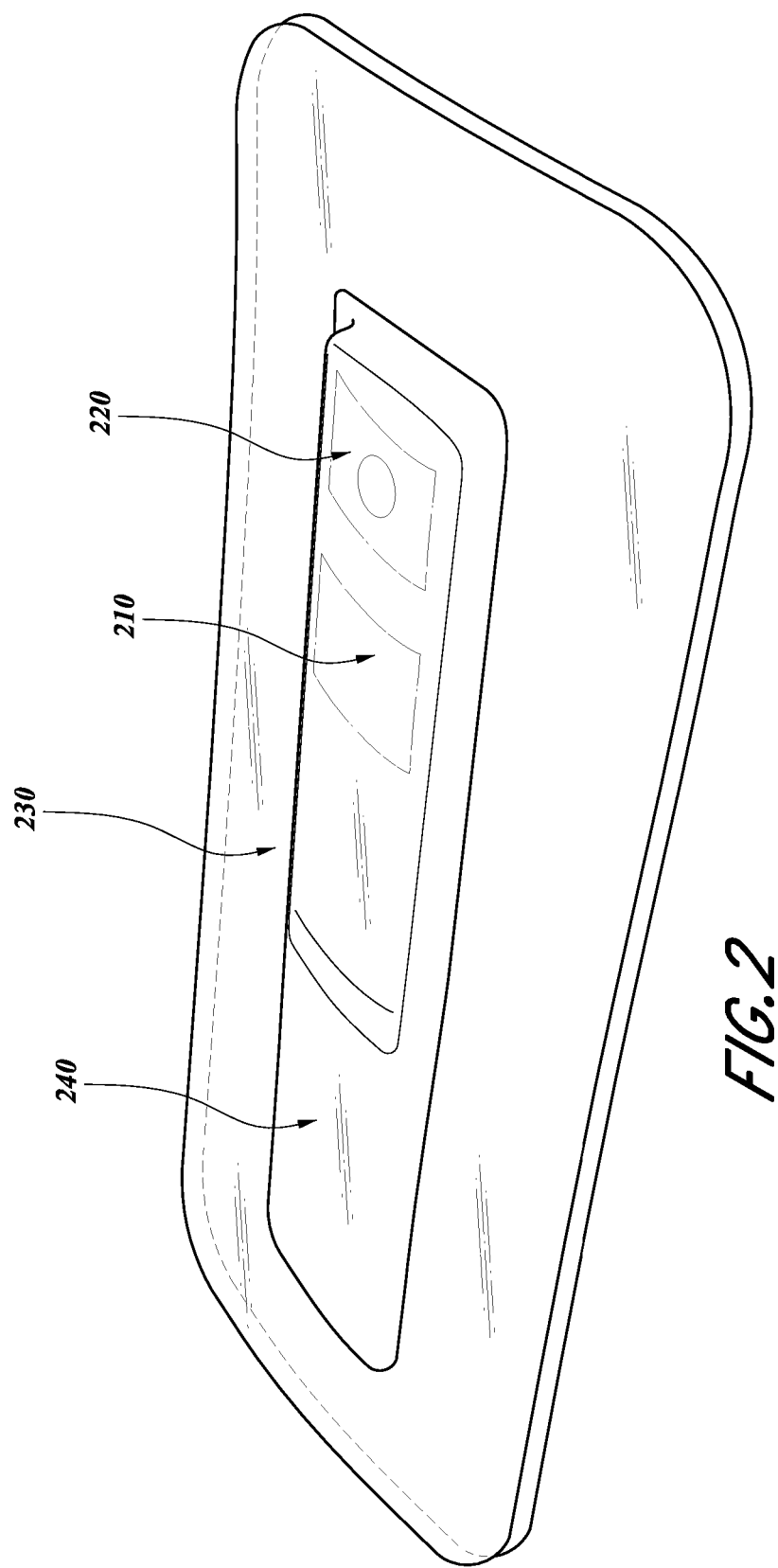
FIG. 2 illustrates an embodiment of a source of negative pressure and battery included within an integrated dressing.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. As is illustrated in FIG. 2, the source of negative pressure and battery can be included within the integrated dressing 200. Although FIG. 2 illustrates the source of negative pressure and battery 210 placed on top of the dressing layer 240 (such as an absorbent layer), the source of negative pressure and one or more components can be incorporated into the dressing differently. The source of negative pressure and the one or more components need not all be incorporated into the dressing in the same manner. For example, a pressure sensor can be positioned below (or closer to the wound) the layer 240 while the source of negative pressure can be positioned on top of the layer 240. The integrated dressing 200 illustrated in FIG. 2 includes a cover layer 230 that can secure the dressing to skin surrounding the wound. The cover layer 230 can be formed of substantially fluid impermeable material, such as film (e.g., plastic film). The cover layer can include an adhesive for securing the dressing to the surrounding skin or wound contact layer.

In some embodiments, the dressing can include the power source and other components, such as electronics, on and/or incorporated into the dressing and can utilize a wound contact layer and a first spacer layer within the dressing. The wound contact layer can be in contact with the wound. The wound contact layer can include an adhesive on the patient facing side for securing the dressing to the skin surrounding the wound or on the top side for securing the wound contact layer to a cover layer or other layer of the dressing. In operation, the wound contact layer can provide unidirectional flow so as to facilitate removal of exudate from the wound while blocking or substantially preventing exudate from returning to the wound. The first spacer layer assists in distributing negative pressure over the wound site and facilitating transport of wound exudate and fluids into the wound dressing. Further, an absorbent layer (such as layer 240) for absorbing and retaining exudate aspirated from the wound can be utilized. In some embodiments, the absorbent includes a shaped form of a superabsorber layer with recesses or compartments for the pump, electronics, and accompanying components. These layers can be covered with one or more layers of a film or cover layer (or a first cover layer). The first cover layer can include a filter set that can be positioned within one of the recesses. The filter can align with one of the at least one recesses of the absorbent layer, and the filter can include hydrophobic material to protect the pump and/or other components from liquid exudates. The filter can block fluids while permitting gases to pass through. Optionally, one or more of the pump, electronics, switch and battery can be positioned on top of the first cover layer as illustrated in FIG. 2. Another section of spacer, a second spacer, can be positioned above and/or surrounding the pump. In some embodiments, the second spacer can be smaller than the first spacer used above the wound contact layer. A section of top film or cover layer (or a second cover layer) is positioned over the top of the second spacer with a second filter associated with or positioned within the second cover layer. In some embodiments, the first and second cover layer can be made of the same material. In some embodiments, the first and second cover layers can be made of different material.

Figure 3A:
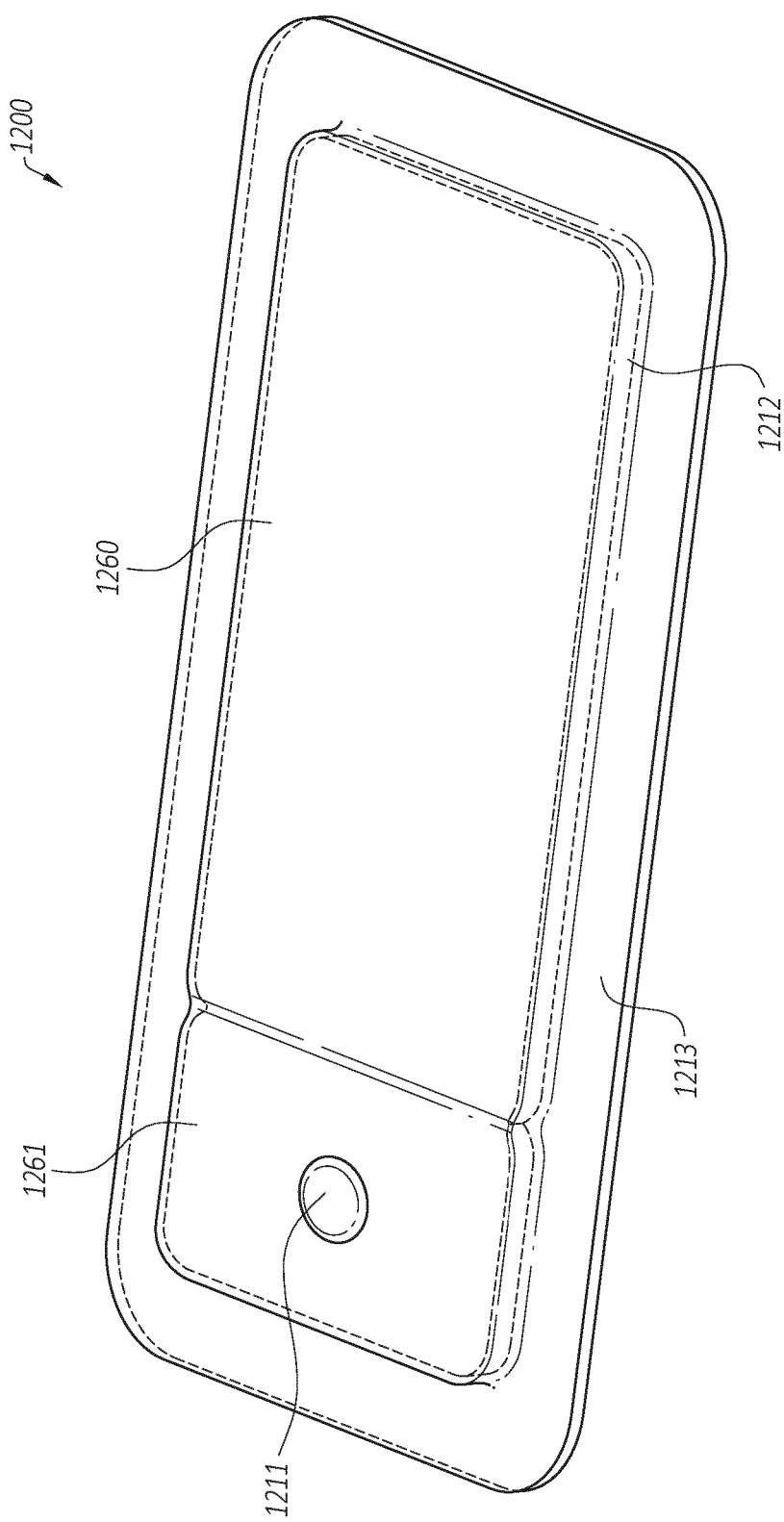
FIGS. 3A-3B illustrate an embodiment of a wound dressing incorporating the source of negative pressure and/or other electronic components within the wound dressing.
Figure 3B:
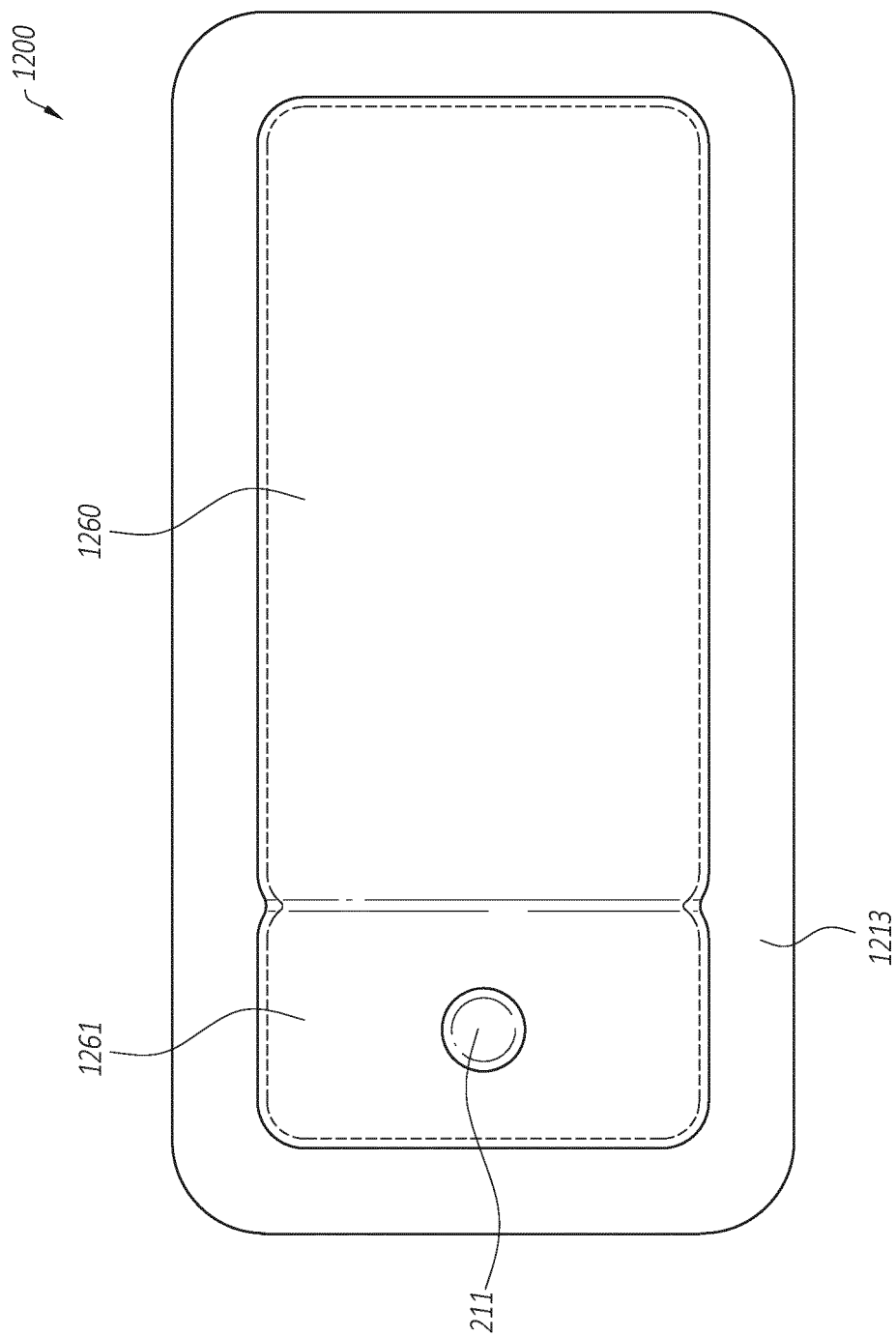
Figure 3C:
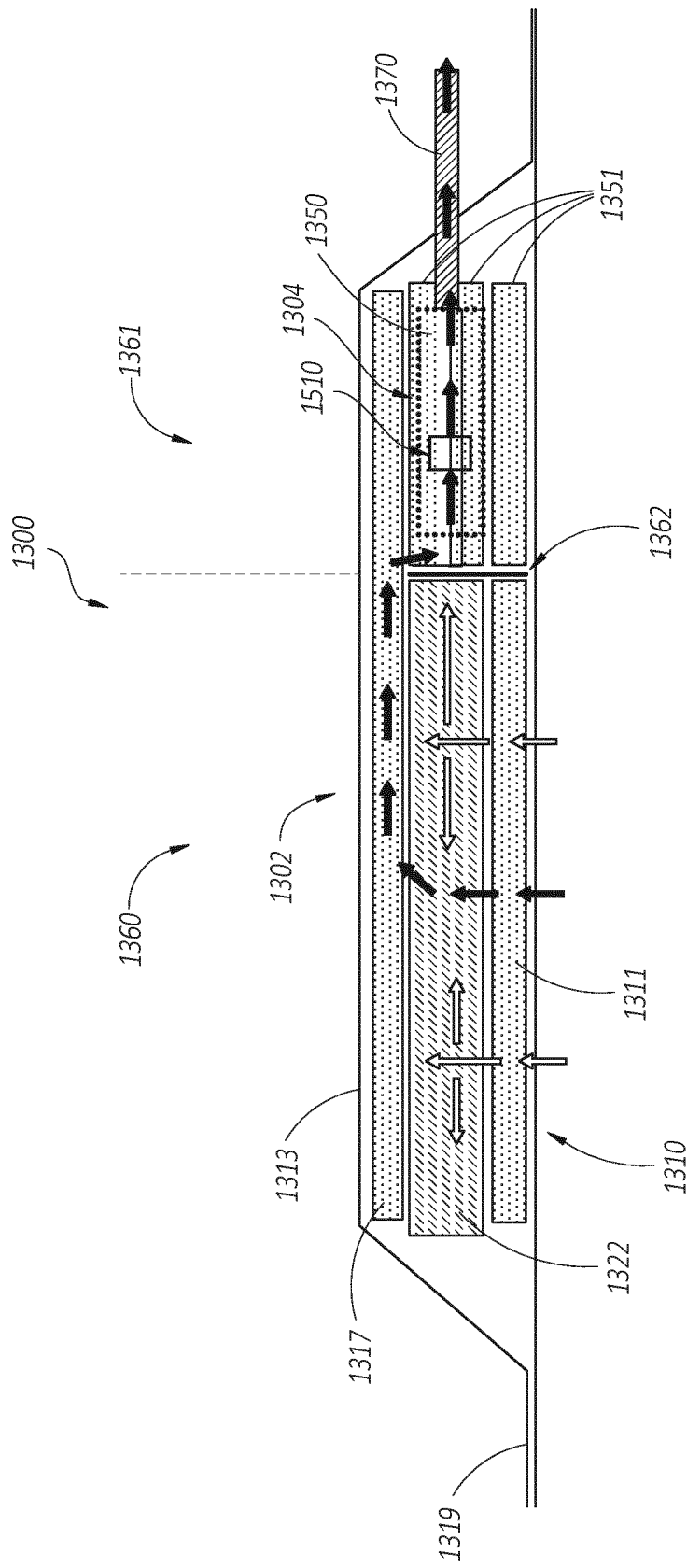
FIG. 3C is a side cross-sectional view of a wound dressing system with one or more embedded electronic components.

In some embodiments, the pump and/or other electronic components can be configured to be positioned adjacent to or next to the absorbent and/or transmission layers so that the pump and/or other electronic components are still part of a single apparatus to be applied to a patient with the pump and/or other electronics positioned away from the wound site. FIGS. 3A-3C illustrates a wound dressing incorporating the source of negative pressure and/or other electronic components within the wound dressing. FIGS. 3A-3C illustrates a wound dressing 1200 with the pump and/or other electronics positioned away from the wound site. The wound dressing can include an electronics area 1261, 1361 and an absorbent area 1260, 1360. The dressing can comprise a wound contact layer 1310 (not shown in FIGS. 3A-3B) and a moisture vapor permeable film or cover layer 1213, 1313 positioned above the contact layer and other layers of the dressing. The wound dressing layers and components of the electronics area as well as the absorbent area can be covered by one continuous cover layer 1213, 1313 as shown in FIGS. 3A-3C.

The dressing can comprise a wound contact layer 1310, a spacer layer 1311, an absorbent layer 1212, 1322, a moisture vapor permeable film or cover layer 1213, 1313 positioned above the wound contact layer, spacer layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound.

The wound contact layer 1310 can be a polyurethane layer or polyethylene layer or other flexible layer which is perforated, for example via a hot pin process, laser ablation process, ultrasound process or in some other way or otherwise made permeable to liquid and gas. The wound contact layer 1310 has a lower surface and an upper surface. The perforations preferably comprise through holes in the wound contact layer 1310 which enable fluid to flow through the layer 1310. The wound contact layer 1310 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 1310 may help maintain the integrity of the entire dressing 1200, 1300 while also creating an air tight seal around the absorbent pad in order to maintain negative pressure at the wound.

Some embodiments of the wound contact layer 1310 may also act as a carrier for an optional lower and upper adhesive layer (not shown). For example, a lower pressure sensitive adhesive may be provided on the lower surface of the wound dressing 1200, 1300 whilst an upper pressure sensitive adhesive layer may be provided on the upper surface of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized it may be helpful to adhere the wound dressing 1200, 1300 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 1311 of porous material can be located above the wound contact layer 1310. As used herein, the terms porous material, spacer, and/or transmission layer can be used interchangeably to refer to the layer of material in the dressing configured to distribute negative pressure throughout the wound area. This porous layer, or transmission layer, 1311 allows transmission of fluid including liquid and gas away from a wound site into upper layers of the wound dressing. In particular, the transmission layer 1311 preferably ensures that an open air channel can be maintained to communicate negative pressure over the wound area even when the absorbent layer has absorbed substantial amounts of exudates. The layer 1311 should preferably remain open under the typical pressures that will be applied during negative pressure wound therapy as described above, so that the whole wound site sees an equalized negative pressure. The layer 1311 may be formed of a material having a three-dimensional structure. For example, a knitted or woven spacer fabric (for example Baltex 7970 weft knitted polyester) or a non-woven fabric could be used.

The spacer layer assists in distributing negative pressure over the wound site and facilitating transport of wound exudate and fluids into the wound dressing. In some embodiments, the spacer layer can be formed at least partially from a three-dimensional (3D) fabric.

In some embodiments, the transmission layer 1311 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 1212,1322 helps lock the liquid away or itself wicks the liquid onwards towards the cover layer 1213, 1313 where it can be transpired.

Preferably, to improve the liquid flow across the transmission layer 1311 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Further, an absorbent layer (such as layer 1212) for absorbing and retaining exudate aspirated from the wound can be utilized. In some embodiments, a superabsorbent material can be used in the absorbent layer 1212. In some embodiments, the absorbent includes a shaped form of a superabsorber layer.

A layer 1212, 1322 of absorbent material is provided above the transmission layer 1311. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 1213, 1313.

The material of the absorbent layer 1212, 1322 may also prevent liquid collected in the wound dressing from flowing freely within the dressing, and preferably acts so as to contain any liquid collected within the dressing. The absorbent layer 1212, 1322 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 1212, 1322 may typically be manufactured from ALLEVYN™ foam, Freudenberg 114-224-4 or Chem-Posite™ 11C-450. In some embodiments, the absorbent layer 1212, 1322 may comprise a composite comprising superabsorbent powder, fibrous material such as cellulose, and bonding fibers. In a preferred embodiment, the composite is an airlaid, thermally-bonded composite.

In some embodiments, the absorbent layer 1212, 1322 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

The wound dressing layers of the electronics area and the absorbent layer can be covered by one continuous cover layer or backing layer 1213. As used herein, the terms cover layer and/or backing layer can be used interchangeably to refer to the layer of material in the dressing configured to cover the underlying dressing layers and seal to the wound contact layer and/or the skin surrounding the wound. In some embodiments, the cover layer can include a moisture vapor permeable material that prevents liquid exudate removed from the wound and other liquids from passing through, while allowing gases through.

The backing layer 1213, 1313 is preferably gas impermeable, but moisture vapor permeable, and can extend across the width of the wound dressing 100. The backing layer 1213, 1313, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 1213, 1313 and a wound site where a negative pressure can be established. The backing layer 1213, 1313 is preferably sealed to the wound contact layer 1310 in a border region around the circumference of the dressing, ensuring that no air is drawn in through the border area, for example via adhesive or welding techniques. The backing layer 1213, 1313 protects the wound from external bacterial contamination (bacterial bather) and allows liquid from wound exudates to be transferred through the layer and evaporated from the film outer surface. The backing layer 1213, 1313 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The electronics area 1261 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 1261 can include a button or switch 1211 as shown in FIGS. 3A-3B. The button or switch 1211 can be used for operating the pump (e.g., turning the pump on/off).

The absorbent area 1260 can include an absorbent material 1212 and can be positioned over the wound site. The electronics area 1261 can be positioned away from the wound site, such as by being located off to the side from the absorbent area 1260. The electronics area 1261 can be positioned adjacent to and in fluid communication with the absorbent area 1260 as shown in FIGS. 3A-3B. In some embodiments, each of the electronics area 1261 and absorbent area 1260 may be rectangular in shape and positioned adjacent to one another.

In some embodiments, additional layers of dressing material can be included in the electronics area 1261, the absorbent area 1260, or both areas. In some embodiments, the dressing can comprise one or more spacer layers and/or one or more absorbent layer positioned above the wound contact layer 1310 and below the cover layer 1213, 1313 of the dressing.

FIG. 3C is a side cross-sectional view of a wound dressing system 1300, according to some embodiments. As shown in FIG. 3C, the wound dressing system 1300 can include a wound dressing 1302 with one or more embedded (also referred to as integrated) electronic components 1350. The wound dressing 1302 can include an absorbent area 1360 and an electronics area 1361. In some embodiments, the electronic components 1350 can be positioned within the wound dressing 1302 in the electronics area 1361, although it should be appreciated that the electronic components 1350 can be integrated with the wound dressing 1302 in any suitable arrangement (e.g., disposed on and/or positioned within the wound dressing 1302, among other arrangements). The electronic components 1350 can optionally include a pump 1304, a power source, a controller, and/or an electronics package, although any suitable electronic component is appreciated. The pump 1304 can be in fluidic communication with one or more regions of the wound dressing 1302, such as, for example, the absorbent area 1360 of the dressing. The absorbent area 1360 and the electronics area 1361 of the wound dressing 1302 can have any suitable arrangement. For example, FIG. 3C illustrates an embodiment of the wound dressing 1302 in which the electronics area 1361 is offset from the absorbent area 1360.

As shown in FIG. 3C, the wound dressing 1302 can include a wound contact layer 1310 and a moisture vapor permeable film or cover layer 1313 that encloses one or both of the absorbent area 1360 and the electronics area 1361. The cover layer 1313 can seal at the perimeter of the cover layer 1319 to the wound contact layer 1310 at the perimeter of the wound contact layer. In some embodiments, the dressing can optionally include an upper spacer layer or first spacer layer 1317 that includes a continuous layer of spacer material positioned below the cover layer 1313 and above the layers of the absorbent area and the layers of the electronics area. The continuous layer of spacer material or upper spacer layer 1317 can enable an air pathway between the two areas of the dressing.

The absorbent area 1360 of the dressing can include a second spacer layer 1311 or lower spacer layer and an absorbent layer 1322 positioned above the wound contact layer 1310. The second spacer layer 1311 can allow for an open air path over the wound site. The absorbent layer 1322 can include a super absorber positioned in the absorbent area 1360 of the dressing. The absorbent layer 1322 can retain wound fluid within thereby preventing fluid passage of wound exudates into the electronics area 1361 of the dressing. The wound fluids can flow through the wound contact layer 1310, to the lower spacer layer 1311, and into the absorbent layer 1322. The wound fluids are then spread throughout the absorbent layer 1322 and retained in the absorbent layer 1322 as shown by the directional arrows for wound fluids in FIG. 3C.

The electronics area 1361 of the dressing can include a plurality of layers of spacer material 1351. In some embodiments, the electronic components 1350 can be embedded within the plurality of layers of spacer material 1351. The layers of spacer material can optionally have recesses or cut outs to embed the electronic components within whilst providing structure to prevent collapse. As described above, the electronic components 1350 can optionally include a pump, a power source, a controller, and/or an electronics package, although any suitable electronic component is appreciated. A partition 1362 can optionally be positioned between the absorbent area 1360 and the electronics area 1361. The partition 1362 can separate the absorbent layer 1322 and lower air flow spacer layer 1311 from the electronic housing segment of the dressing in the electronic area. The partition 1362 can prevent wound fluid (e.g., wound exudate) from entering the electronic housing section of the dressing. In some embodiments, the partition can be a non-porous dam or other structure. The non-porous dam 1362 can include a cyanoacrylate adhesive bead or a strip of silicone. The air pathway through the dressing is shown in FIG. 3C by directional arrows. The air flows through the wound contact layer 1310, the lower spacer layer 1311, and the absorbent layer 1322 and into the first spacer layer 1317.

The air can travel horizontally through the first spacer layer 1317 over and around the partition 1362 into the electronics area of the dressing.

As shown in FIG. 3C, the wound dressing system 1300 can include a fluid ingress inhibition component 1510 in fluid communication with a pump 1304. The component 1510 can allow gas (e.g., air) but inhibit liquid (e.g., wound exudate) from passing through. In some embodiments, the wound dressing layers and the component 1510 can be used with or without the optional partition 1362. The component 1510 can provide a plurality of flow paths between an interior of the wound dressing 1302 and the pump 1304 so that occlusion (e.g., from wound exudate) of the pump 1304 is inhibited. Advantageously, should any of the plurality of flow paths become occluded, one or more of the other flow paths of the plurality will be able to maintain an uninterrupted flow path between the wound dressing 1302 and the pump 1304. Such flow path redundancy can advantageously make operation of wound dressing systems 1300 more stable and reliable. In this way, the component 1510 can allow a more stable target pressure to be delivered to a wound site by ensuring that there is an open flow path between the wound dressing 1302 and the pump 1304 and by inhibiting occlusions that would otherwise cause the target pressure to be more varied. In some embodiments, the surface area of the component 1510 can advantageously increase the contact area between the pump 1304 and the wound dressing 1302, thereby providing more flow paths into the inlet of the pump 1304 for the same sized inlet. In some embodiments, the wound dressing system 1300 can include two or more components 1510. For example, in some embodiments, the wound dressing system 1300 can include between two and ten or more components 1510. The exact number used may depend on a number of factors, including the size of the wound site and the wound exudate discharge rate, in addition to the space constraints of the wound dressing, as well as other factors.

In some embodiments, the component 1510 can be made of a hydrophobic material that repels wound exudate, thereby inhibiting the ingress of fluid into the component 1510 and ultimately the pump 1304. In some embodiments, component 1510 can be a hydrophobic coated material. In some embodiments, the component 1510 can be made of a porous material. The pores can be small enough to inhibit the ingress of fluid through the component 1510 due to capillary action (i.e., from surface tension of the wound exudate against the component 1510) and the pressure differential between the environment and the wound dressing, but large enough to permit the passage of air. For example, in some embodiments, the component 1510 can be made of a material that has a pore size in the range of approximately 20 microns to approximately 100 microns. For example, in some embodiments, the material of the component 1510 can have a pore size of approximately 30 microns. In some embodiments, the material of the component 1510 can have a pore size of approximately 10 microns. However, it will be understood that any suitable pore size is appreciated. In some embodiments, the component can be a foam or a foam-like material. The hydrophobic nature of the material of the component 1510 and/or its pore size can function to inhibit the flow of wound exudate from the wound dressing 1302 to the pump 1304. The component 1510 thereby inhibits the pump 1304 in the wound dressing system 1300 from discharging wound exudate from the wound dressing 1302.

As described above, the material of the component 1510 can be porous. The plurality of flow paths through the component 1510 can be defined by a series of sequentially connected pores formed in the material of the component 1510, beginning with pore(s) in fluid communication with an interior of the wound dressing 1302 and positioned on the exterior of the component 1510 and ending with pore(s) in fluid communication with the pump 1304 and positioned on the interior of the component 1510. Pores advantageously provide flow path redundancy because of their lattice arrangement and interconnected structure. The plurality of flow paths through the component 1510 that connect the first pore(s) in fluid communication with an interior of the wound dressing 1302 and the last pore(s) in fluid communication with the pump 1304 can be straight and/or tortuous. A group of open pores can effectively create one or more larger flow channels through the component 1510 that can sizably adjust as one or more occlusions materialize inside and/or outside the component 1510. In some embodiments, one or more pores can define one or more overlapping flow paths. For example, if one or more adjacent and/or neighboring pores of an open pore become occluded by wound exudate, the open pore can maintain an open path from the wound dressing 1302 to the pump 1304 by helping to redefine one or more flow paths around the one or more occluded pores. It will be appreciated that the plurality of flow paths through the component can be formed with any suitable structure. For example, in addition to or in lieu of pores, the plurality of flow paths can be formed by one or more channels extending through the component 1510.

Figure 4A:
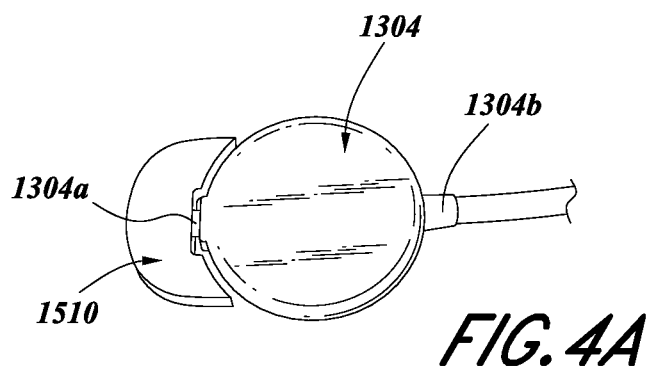
FIG. 4A illustrates an embodiment of a component directly coupled to the pump inlet.
Figure 4B:
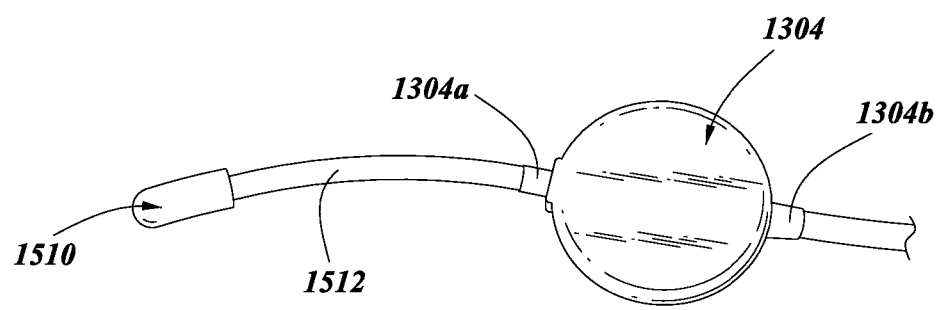
FIGS. 4B and 4C illustrate an embodiment of components indirectly coupled to the pump inlet via an intermediate tubular member.
Figure 4C:
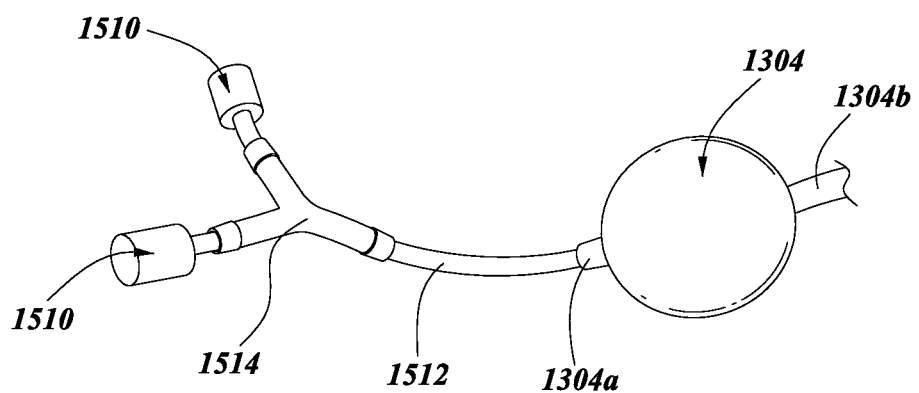

In some embodiments, the component 1510 can be a porous polymer component. The porous polymer component can be machined and/or molded (e.g., injection molded) into any suitable shape. For example, FIGS. 4A-4C illustrate three differently shaped porous polymer components 1510 in fluid communication with a pump 1304. FIG. 4A illustrates a crescent-shaped component 1510. FIG. 4B illustrates a thimble-shaped component 1510 with a cylindrical body and rounded terminal end. FIG. 4C illustrates two thimble-shaped components 1510 with cylindrical bodies and flat terminal ends. Each of the components 1510 can allow gas (e.g., air) to pass from various points in the wound dressing (not shown) into the pump 1304 through one or more of a plurality of flow paths. The porous polymer component can be formed from POREX®, PORVAIR®, or any other suitable hydrophobic material, such as, for example, polyethylene and/or polypropylene, among others. In some embodiments, the porous polymer component can be formed from PORVAIR Vyon® porous polymer. As described above, the material of the component 1510 can be made of a material that has a pore size in the range of approximately 5 microns to approximately 100 microns (e.g., 5 microns, 100 microns). For example, in some embodiments, the material of the component 1510 can have a pore size of approximately 30 microns (e.g., 30 microns). In some embodiments, the material of the component 1510 can have a pore size of approximately 10 microns (e.g., 10 microns). However, it will be understood that any suitable pore size is appreciated.

The components 1510 shown in FIGS. 4A-4C are shown directly or indirectly coupled to an inlet 1304a of the pump 1304. For example, FIG. 4A illustrates a component 1510 directly coupled to the pump inlet 1304a and FIGS. 4B and 4C illustrate components 1510 indirectly coupled to the pump inlet 1304a via an intermediate tubular member 1512. FIG. 4C also illustrates a Y-shaped splitter 1514 that connects the two components 1510 to the intermediate tubular member 1512. In some embodiments, the intermediate tubular member 1512 and the Y-shaped splitter 1514 in FIG. 4C can be a unitary piece. The internal diameter of the intermediate tubular member 1512 and the Y-shaped splitter 1514 can be in the range of approximately 1 mm to approximately 3 mm, such as for example, 2 mm. Of course, it will be understood that any suitable arrangement and structure is appreciated.

Although not shown in FIGS. 4A-4C, a non-return valve and/or an exhaust system can be coupled to the pump outlet 1304b. Additional disclosure relating to exhaust systems and non-return valves can be found in International Application No. PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING," which is hereby incorporated by reference in its entirety, the disclosure of which is considered to be part of the present application. Advantageously, the component 1510 can inhibit wound exudate from being drawn from the wound site through the pump and into the non-return valve and/or exhaust system.

Figure 5A:
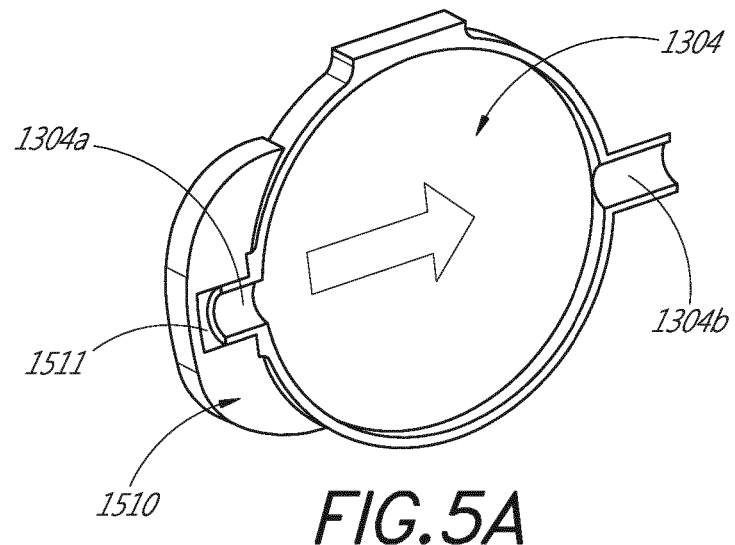
FIGS. 5A-5C illustrate cross-sectional views of the corresponding components shown in FIGS. 4A-4C.
Figure 5B:
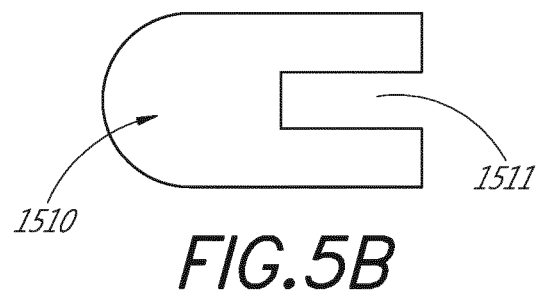
Figure 5C:
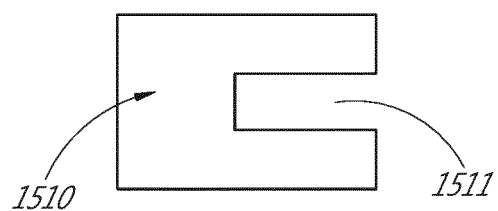

FIGS. 5A-5C illustrate cross-sectional views of the corresponding components 1510 shown in FIGS. 4A-4C, respectively. For example, FIG. 5A illustrates the component 1510 of FIG. 4A having a port 1511 that receives a portion of the pump inlet 1304a. FIGS. 5B and 5C similarly illustrate components 1510 having ports 1511. In some embodiments, the component 1510 can receive a portion of and/or be bonded to the member to which it connects (e.g., a pump inlet). For example, in some embodiments, the component 1510 in FIG. 5A can be bonded (e.g., glued or heat welded) to the pump inlet 1304a. In some embodiments, the component 1510 in FIG. 5A can freely slide over the pump inlet 1304a. One or more surrounding features of the wound dressing system 1300 can help keep the component in place (e.g., compression between the cover layer 1313 and the wound contact layer 1310 shown in FIG. 3C).

Figure 6A:
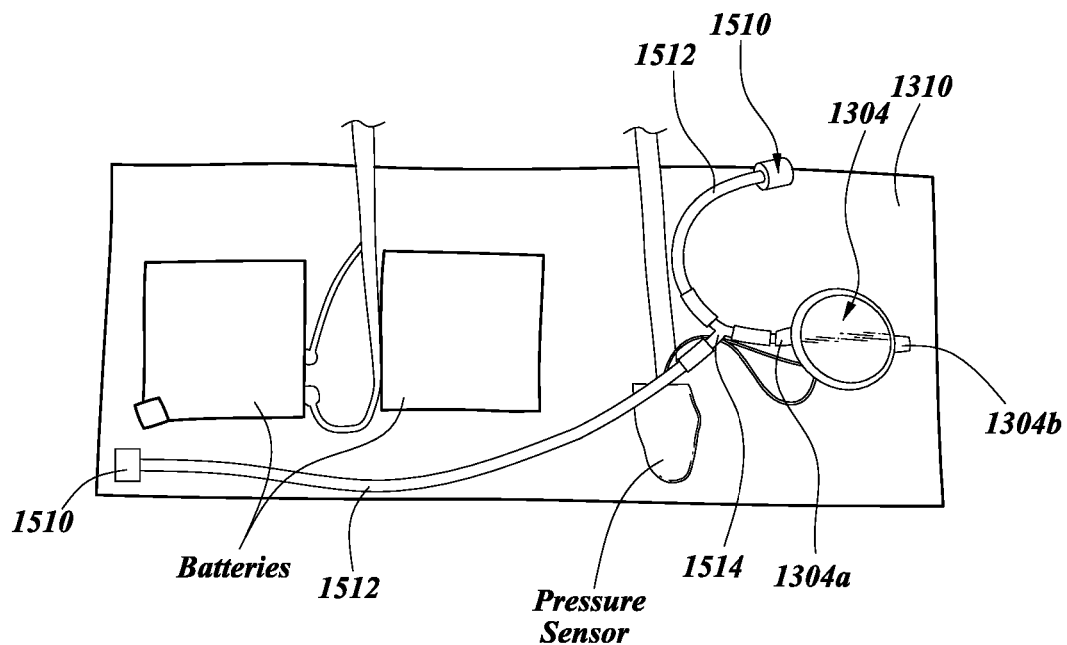
FIGS. 6A and 6B illustrate a fluid ingress inhibition system similar to the system.
Figure 6B:
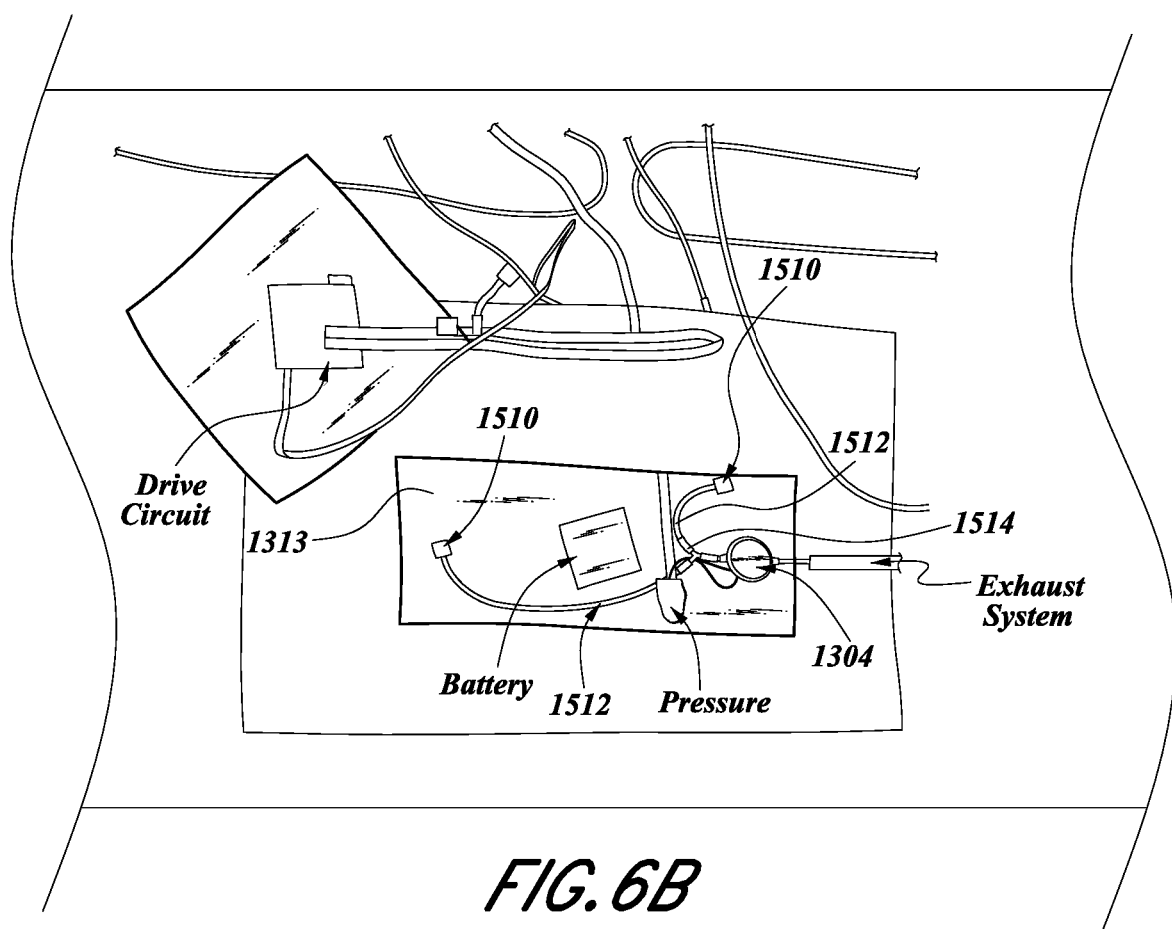

FIGS. 6A and 6B illustrate a fluid ingress inhibition system similar to the system of FIG. 5C sitting on top of a wound dressing padding or other wound dressing layer. FIG. 6A illustrates two components 1510 sitting on top of a layer of the dressing with the cover layer 1313 removed. FIG. 6B shows FIG. 6A with the cover layer 1313 or other dressing layer drawn down onto the various internal components, including the two components 1510.

In some embodiments, the component 1510 does not reduce the pump flow rate by more than 50 mL/min. For example, in some embodiments, the component 1510 can reduce the pump flow rate in the range of 15 mL/min to 35 mL/min (e.g., from 21 mL/min to 31 mL/min). In some embodiments, the component 1510 does not reduce the free performance of the pump by more than 10%. For example, in some embodiments, the component 1510 can reduce the free performance of the pump in the range of 4% to 6%.

In some embodiments, the component 1510 can be a micro porous membrane attached to a pump inlet. In some embodiments, the membrane can be formed into the shape of a pouch to fit over and attach to the pump inlet. A 3d spacer (e.g., fabric) can be disposed in the pouch to inhibit the membrane from collapsing. In some embodiments, the pouch can be elongate in form, but it will be appreciated that the pouch can take on any suitable form. The membrane can be hydrophobic to repel fluid (e.g., wound exudate) and have a porosity that inhibits fluid ingress into the pump inlet due to capillary action. For example, in some embodiments, the micro porous membrane can be made of Versapore having a 0.2 μm pore size (Pall).

In some embodiments, the component 1510 can be one or more lengths of fine bore tubing with a plurality of holes disposed along their lengths. The one or more lengths of fine bore tubing can form one or more loops between a pump inlet and a wound dressing. As another example, the one or more lengths of fine bore tubing can extend from the pump inlet to one or more different points in the wound dressing, similar to the way in which the two components 1510 in FIGS. 6A and 6B are positioned at two different points in the wound dressing. The size of the bore in the tubing can have an internal diameter such that the tubing resists collapse under reduce pressure.

In some embodiments, the component 1510 is designed so that a significant pressure drop is avoided by its use. In this way, the component 1510 prevents the pump 1304 from having to work harder and consume more power from any added resistance it may add to the flow path from the wound dressing to the environment through the pump 1304.

FIGS. 7A and 7B illustrate embodiments of an electronics unit 1700 including a pump 1704 and a component 1710 directly coupled to the pump inlet 1704a. FIG. 7A illustrates the top view of the electronics unit. FIG. 7B illustrates a bottom or wound facing surface of the electronics unit. The electronics unit 1700 can include a pump and other electronic component such as power source(s), sensor(s), connector(s), circuit board(s), user interface component(s) (such as button(s), switch(es), speaker(s), screen(s), etc.) and the like. In some embodiments, the electronics unit of FIGS. 7A-7B can be embedded into the electronics area 1361 of the wound dressing as one unit.

In some embodiments, the component 1710 can be pushed onto the pump inlet. This can be a friction fit. The port of the component 1710 that receives a portion of the pump inlet can be sized and shaped to be a complementary fit around the pump inlet. In some embodiments, the component 1710 can be bonded onto the pump inlet using a silicone sealant or any other sealant or sealing technique. In some embodiments, the electronics unit can be embedded within layers of the dressing in the electronics area 1361. In some embodiments, the layers of the dressing in the electronics area 1361 can include cutouts or recesses into which the electronics unit 1700 can be placed.

Figure 8:
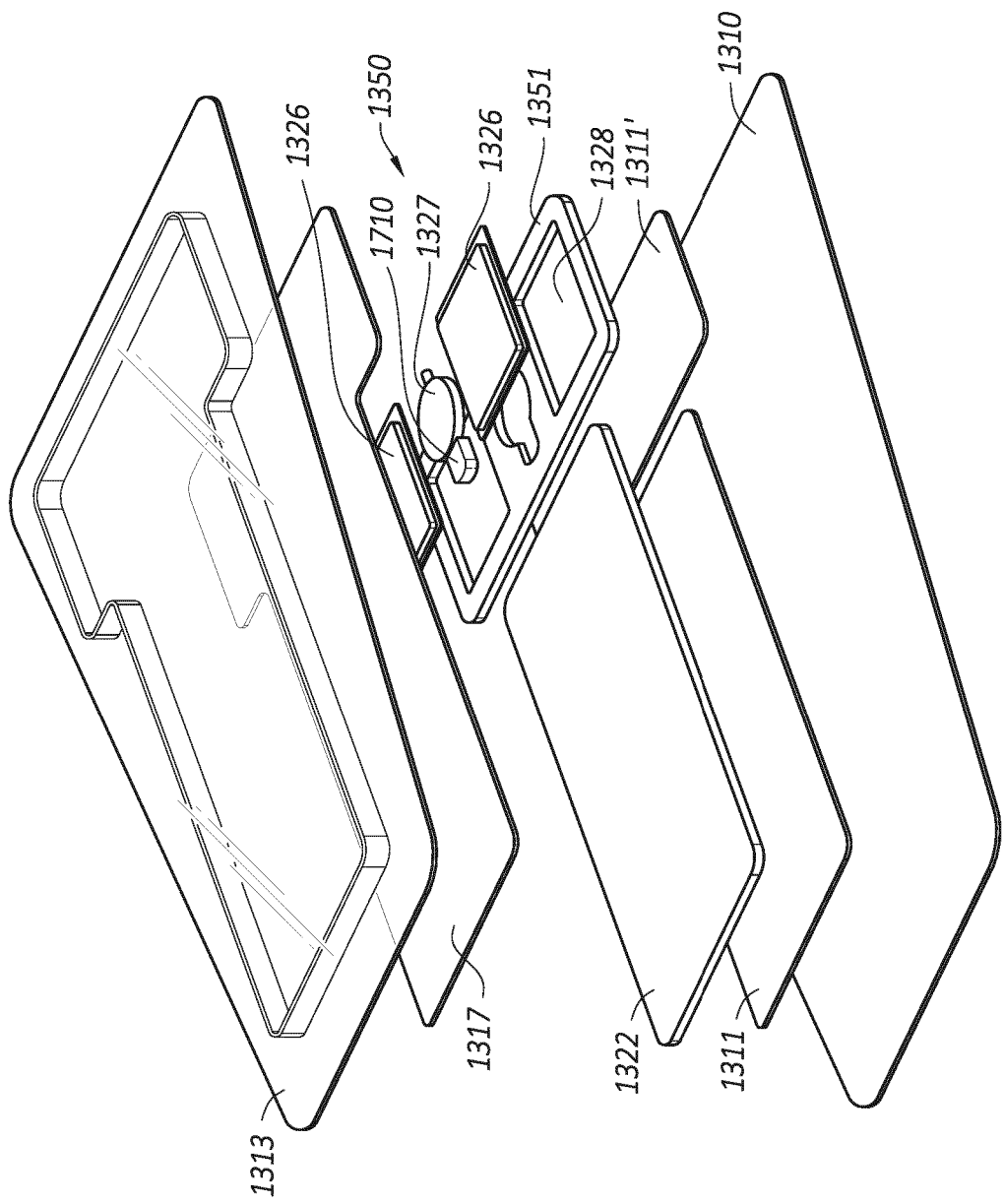
FIG. 8 illustrates an embodiment of the layers of a wound dressing incorporating the source of negative pressure and/or other electronic components within the wound dressing.

FIG. 8 illustrates the wound dressing layers for embedding or integrating an electronics unit. As illustrated in FIG. 8, the dressing can include a wound contact layer 1310 for placing in contact with the wound. Lower spacer layers 1311 and 1311' are provided above the wound contact layer 1310. In some embodiments, the spacer layer 1311 can be a separate layer from spacer layer 1311' as shown in FIG. 8. In other embodiments, the lower spacer layers 1311 and/or 1311' can be a continuous layer of spacer material that is below both the electronics area and the absorbent area. The lower spacer layers 1311 and 1311' can assist in distributing pressure evenly to the wound surface and/or wicking fluid away from the wound. An absorbent layer 1322 can be positioned above the lower spacer layer 1311 and/or 1311'. A dressing layer 1351 can include cutouts or recesses 1328 for embedding the electronic components 1350 within the layer 1351. In some embodiments, the layer 1351 can be an absorbent material. In some embodiments, the dressing layer 1351 and absorbent layer 1322 can be one continuous piece of absorbent material. Alternatively, in some embodiments, the layer 1351 can be a spacer layer or transmission material. In some embodiments, the cutouts or recesses 1328 can be sized and shaped to embed a pump 1327, power source 1326, and/or other electronic components of the electronics unit. In some embodiments, the pump 1327, power source 1326, and/or other electronic components can be incorporated into the cutouts or recesses 1328 as individual components or as an electronic assembly as shown in FIGS. 7A-7B. An upper layer 1317 optionally can be provided above the absorbent layer 1322, layer 1351, and/or electronic components 1350. A cover layer or backing layer 1313 can be positioned over the upper spacer layer. In some embodiments, when the upper layer 1317 is not used, the cover layer or backing layer 1313 can be provided above the absorbent layer 1322, layer 1351, and/or electronic components 1350. The backing layer 1313 can form a seal to the wound contact layer 1310 at a perimeter region enclosing the spacer layers 1311, 1311', and 1317, the absorbent layer 1322, layer 1351, and electronic components 1350. In some embodiments, the backing layer 1313 can be a flexible sheet of material that forms and molds around the dressing components when they are applied to the wound. In other embodiments, the backing layer 1313 can be a material that is preformed or premolded to fit around the dressing components as shown in FIG. 8.

The component 1710 can be provided on the inlet of the pump 1327. In some embodiments, the hydrophobicity of the component 1710 can keep the inlet to the pump free of exudate. In some embodiments, the component 1710 can be in contact with and/or in fluid communication with superabsorbent and/or absorbent material. In this configuration, the component 1710 can prevent liquid from being pulled through to the inlet of the pump when negative pressure is applied. The component 1710 can be made of a material with a pore size larger than the pore size of traditional hydrophobic filters and liquid could get through if the material of the component were by itself in contact with water. However, the hydrophobicity of the hydrophobic component 1710 with a pore size as described herein can be in contact with the superabsorber and/or absorbent material and can prevent exudate from being pulled through the inlet of the pump when negative pressure is applied.

Figure 9B:
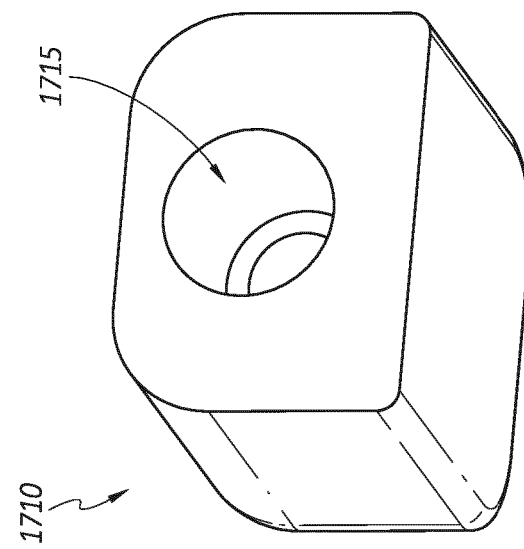
FIG. 9 illustrates an embodiment of a component with a port for coupling to the pump inlet.
Figure 9A:
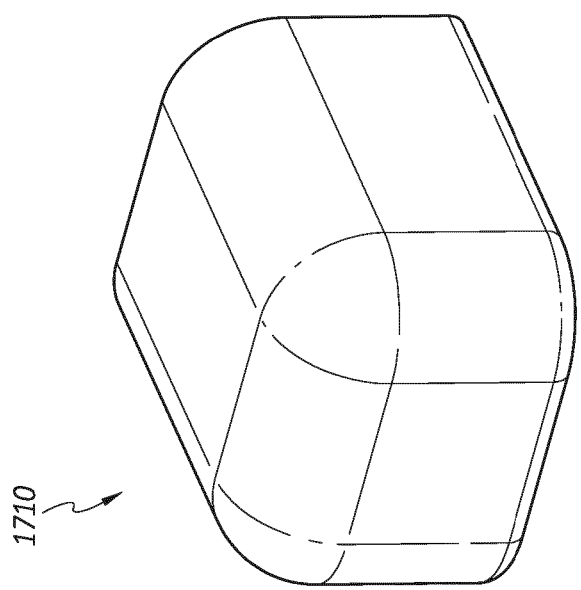

FIG. 9A-9B illustrates an embodiment of a component 1710 with a port 1715 for coupling to the pump inlet. The port 1715, similar to port 1511 of FIGS. 5A-5C, is shaped to receive a portion of the pump inlet 1304a. In some embodiments, the shape of the pump inlet 1304a can be tubular or cylindrical as shown in the cross-section of the pump inlet 1304a in FIG. 5A. In some embodiments, the component 1710 can receive a portion of and/or be bonded to the member to which it connects (e.g., a pump inlet). For example, in some embodiments, the component 1710 can be bonded (e.g., glued or heat welded) to the pump inlet 1304a. In some embodiments, the component 1710 can freely slide over the pump inlet 1304a. One or more surrounding features of the wound dressing system can help keep the component in place (e.g., compression between the cover layer and the wound contact layer).

In some embodiments, the component 1710 can have a 3-dimensional shape and circumferentially surrounds the pump inlet. The 3-dimensional shaped component 1710 can have a width, height, and/or length dimension that is greater than the width, height, and/or length of the pump inlet 1304a. In some embodiments, the component 1710 can be a cuboid or generally cuboid shape as shown in FIGS. 9A and 9B. For example, the component 1710 may have a flat pump-facing surface through which the port 1715 extends, with one or more beveled edges and/or corners. In some embodiments, the 3-dimensional component can circumferentially surround the pump inlet when the pump inlet is inserted into the port 1715 of the component 1710. By circumferentially surrounding the pump inlet, the 3-dimensional component can provide a surface area larger than the surface area available at the pump inlet 1304a. The larger surface area can provide a plurality of flow paths within the component 1710. This can allow air to be drawn through a portion of the component 1710 even when another portion of the component 1710 is surrounded by fluid or otherwise blocked.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wound dressing apparatus comprising:
 a wound dressing configured to be positioned over a wound site, the wound dressing comprising:
  a wound contact layer configured to be positioned in contact with a wound;
  a first area and a second area positioned adjacent to the first area, wherein the first area comprises an absorbent material and the second area is configured to receive a negative pressure source; and
  a cover layer configured to cover and form a seal over the wound contact layer, the first area, and the second area;
 a negative pressure source disposed on or positioned within the second area of the wound dressing, the negative pressure source comprising an inlet and an outlet and being operable to apply negative pressure to the wound site; and
 a component in fluid communication with the inlet, the component defining a plurality of flow paths between an interior of the wound dressing and the inlet such that occlusion of the inlet is inhibited,
 wherein the component is in fluid communication with the absorbent material and configured to inhibit flow of wound exudate from the wound site into the inlet,
 wherein the component comprises a port configured to receive at least a portion of the inlet, wherein at least a portion of the plurality of flow paths of the component is configured to directly contact a portion of the inlet received by the port.

2. The wound dressing apparatus of claim 1, wherein the component comprises a hydrophobic material configured to repel wound exudate.

3. The wound dressing apparatus of claim 1, wherein the component comprises a material having a pore size configured to resist ingress of wound exudate due to capillary action.

4. The wound dressing apparatus of claim 1, wherein the component comprises one or more porous polymer molded components.

5. The wound dressing apparatus of claim 4, wherein the polymer comprising the one or more porous polymer molded components is hydrophobic and has a pore size in the range of approximately 20 microns to approximately 40 microns.

6. The wound dressing apparatus of claim 5, wherein the pore size is approximately 30 microns.

7. The wound dressing apparatus of claim 4, wherein the polymer comprising the one or more porous polymer molded components is hydrophobic and has a pore size in the range of approximately 5 microns to approximately 40 microns.

8. The wound dressing apparatus of claim 7, wherein the pore size is approximately 10 microns.

9. The wound dressing apparatus of claim 4, wherein the polymer is one of hydrophobic polyethylene or hydrophobic polypropylene.

10. The wound dressing apparatus of claim 4, wherein each of the one or more porous polymer molded components provides an increased contact area to the interior of the wound dressing.

11. The wound dressing apparatus of claim 4, wherein the one or more porous polymer components is one of crescent-shaped, thimble-shaped, or cuboid or generally cuboid shaped.

12. The wound dressing apparatus of claim 4, wherein the one or more porous components comprise curved or beveled corners and/or edges.

13. The wound dressing apparatus of claim 4, wherein the one or more porous polymer components is configured to attach to at least one of the inlet and an end of a tubular extension in fluid communication with the inlet and the interior of the wound dressing.

14. The wound dressing apparatus of claim 1, wherein the component comprises one or more micro porous membranes attached to the inlet.

15. The wound dressing apparatus of claim 14, further comprising a spacer material disposed within the membrane, the spacer material configured to inhibit the membrane from collapsing.

16. The wound dressing apparatus of claim 14, wherein the micro porous membrane comprises a 0.2 micron pore size.

17. The wound dressing apparatus of claim 1, wherein the component comprises one or more lengths of fine bore tubing defining a plurality of holes along their lengths.

18. The wound dressing apparatus of claim 17, wherein the one or more lengths of fine bore tubing forms one or more loops between the inlet and the wound dressing.

19. The wound dressing apparatus of claim 17, wherein the one or more lengths of fine bore tubing extend from the inlet to one or more different points in the wound dressing.

20. The wound dressing apparatus of claim 1, wherein the negative pressure source is a micro pump.

21. The wound dressing apparatus of claim 20, further comprising a controller configured to control the operation of the micro pump to apply negative pressure to the wound site.

22. The wound dressing apparatus of claim 1, wherein the absorbent material is configured to absorb wound exudate.

23. The wound dressing apparatus of claim 1, wherein the component is attached to the inlet.

24. The wound dressing apparatus of claim 1, wherein the component is fitted to the inlet.

25. A wound dressing apparatus comprising:
- a wound dressing configured to be positioned over a wound site, the wound dressing comprising:
  - a wound contact layer configured to be positioned in contact with a wound;
  - a first area and a second area positioned adjacent to the first area, wherein the first area comprises an absorbent material and the second area is configured to receive a negative pressure source; and
  - a cover layer configured to cover and form a seal over the wound contact layer, the first area, and the second area;
- a negative pressure source disposed on or positioned within the second area of the wound dressing, the negative pressure source comprising an inlet and an outlet and being operable to apply negative pressure to the wound site; and
- a porous polymer molded component comprising a port configured to receive at least a portion of the inlet and fitted to the inlet such that the porous polymer molded component is in fluid communication with the inlet and an interior of the wound dressing, the porous polymer molded component defining a plurality of flow paths between the interior of the wound dressing and the inlet such that occlusion of the inlet is inhibited, wherein at least a portion of the plurality of flow paths of the porous polymer molded component is configured to directly contact a portion of the inlet received by the port, wherein the porous polymer molded component is in fluid communication with the absorbent material and configured to inhibit flow of wound exudate from the wound site into the inlet.

* * * * *